United States Patent [19]

Aoki et al.

[11] Patent Number: 4,549,902

[45] Date of Patent: Oct. 29, 1985

[54] SALTS OF DERIVATIVES OF N-(TETRAHYDROBENZOTHIAZOLYLCAR-BAMOYL)OXAMIC ACID AND HERBICIDAL COMPOSITION CONTAINING THE SAME AS ACTIVE INGREDIENT

[75] Inventors: Katsumichi Aoki; Takafumi Shida; Hideo Arabori; Satoru Kumazawa; Susumu Shimizu; Takeo Watanabe; Yohichi Kanda; Keigo Satake; Shiro Yamazaki; Hiroyasu Shinkawa; Tsuneaki Chida, all of Iwaki, Japan

[73] Assignee: Kureha Kagaku Kogyo Kabushiki Kaisha, Tokyo, Japan

[21] Appl. No.: 597,269

[22] Filed: Apr. 6, 1984

[30] Foreign Application Priority Data

Apr. 8, 1983 [JP] Japan ................................. 58-61928

[51] Int. Cl.$^4$ .................... C07D 277/82; A01N 47/36
[52] U.S. Cl. ......................................... 71/90; 548/163
[58] Field of Search ............................. 548/163; 71/90

[56] References Cited

FOREIGN PATENT DOCUMENTS 110578 7/1983 Japan ................................. 548/163

Primary Examiner—Robert Gerstl
Attorney, Agent, or Firm—Austin R. Miller

[57] ABSTRACT

Disclosed herein are a salt of a derivative of N-(tetrahydrobenzothiazolylcarbamoyl)oxamic acid, represented by the formula:

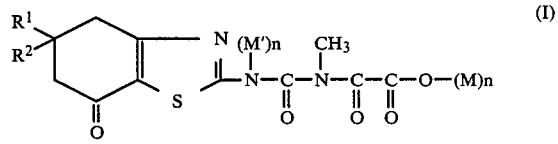

wherein $R^1$ represents a straight-chain alkyl group having one to six carbon atoms, branched-chain alkyl group having up to and including six carbon atoms, cyclic alkyl group having up to and including six carbon atoms or a phenyl group; $R^2$ represents a hydrogen atom or a methyl group; M represents an alkali metal atom or an alkaline earth metal atom; n is 1 when M is an alkali metal atom and n is ½ when M is an alkaline earth metal atom and M' is a hydrogen atom or the same as M, and a herbicidal composition containing the same as an active ingredient.

12 Claims, 13 Drawing Figures

SALTS OF DERIVATIVES OF N-(TETRAHYDROBENZOTHIAZOLYLCARBAMOYL)OXAMIC ACID AND HERBICIDAL COMPOSITION CONTAINING THE SAME AS ACTIVE INGREDIENT

DETAILED DESCRIPTION OF THE INVENTION

Figure 1:
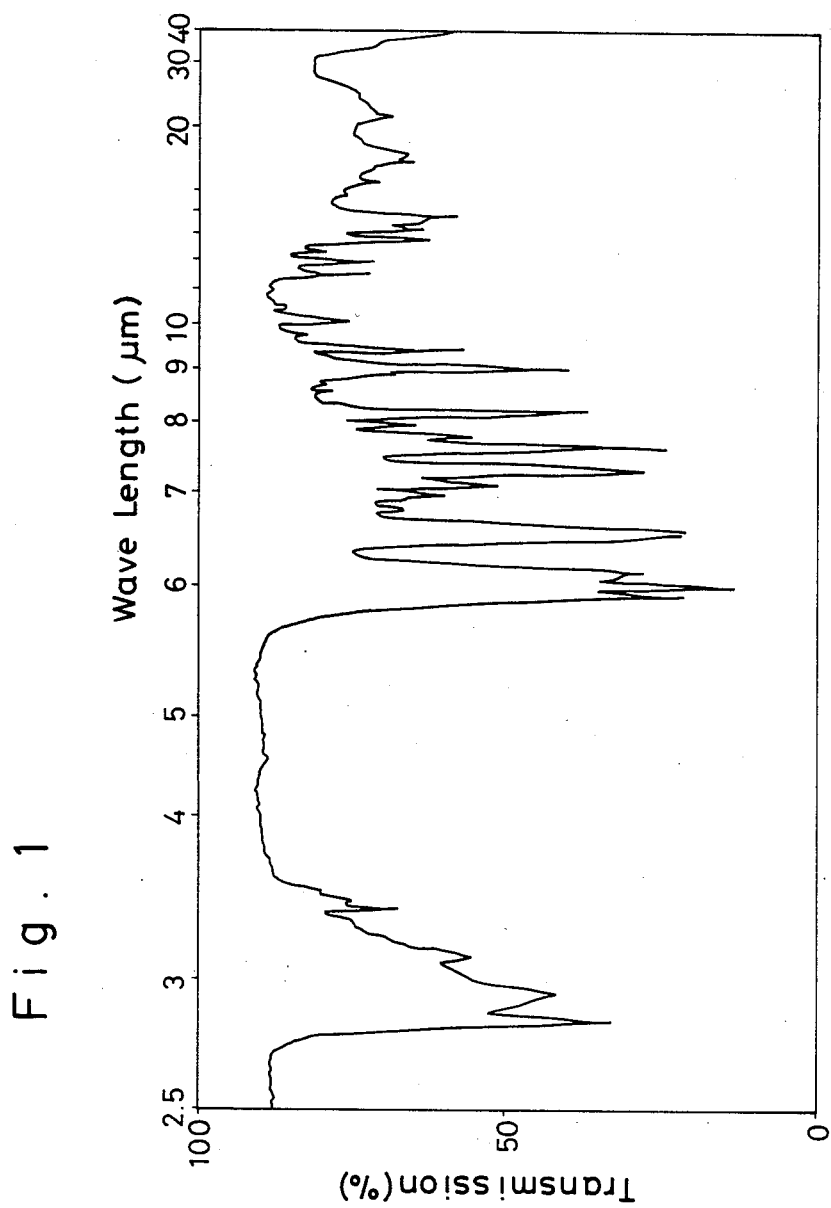

The present invention relates to a salt of a derivative of N-(tetrahydrobenzothiazolylcarbamoyl)oxamic acid represented by the formula:

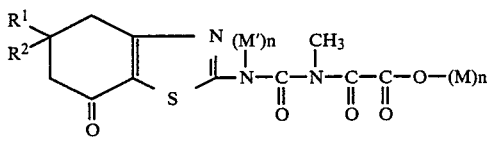

wherein $R^1$ represents a straight-chain alkyl group having one to six carbon atoms, branched-chain alkyl group having up to and including six carbon atoms, cyclic alkyl group having up to and including six carbon atoms or a phenyl group; $R^2$ represents a hydrogen atom or a methyl group; M represents an alkali metal atom or an alkaline earth metal atom; and n is 1 when M is an alkali metal atom and n is ½ when M is an alkaline earth metal atom and M' is a hydrogen atom or the same as M, and a herbicidal composition containing the same as an active ingredient.

The present inventors have studied for finding out a compound showing an excellent activity in selective control of the weeds such as Echinochloa crus-galli, Poa annua, Cardamine flexuosa, Portulaca oleracea, etc. without giving any phytotoxicity (damage) to crop plants such as rice, wheat, soybean and maize, and as a result, they have found out that a derivative of a salt of N-(tetrahydrobenzothiazolylcarbamoyl)oxyamic acid represented by the formula (I) shows an excellent herbicidal activity for practical control of the weeds, and have attained to the present invention.

The compounds represented by the formula (I) are novel compounds, and of course, the physiological properties thereof have never been known. According to the herbicidal tests consisting essentially of foliar application and soil treatment, every one of the derivatives of a salt of N-(tetrahydrobenzothiazolylcarbamoyl)oxamic acid according to the present invention (hereinafter referred to as "the present compounds") shows an excellent herbicidal activity on broad-leaved weeds, for instance, Stellaria media, Cardamine flexuosa and Portulaca oleracea, Cyperaceous weeds, for instance, Cyperus iria and Gramineous weeds, for instance, those belonging to the genus Echinochloa and Poa annua, and particularly shows a strong herbicidal activity when applied on leaves and stems of these weeds. The application of the herbicidal composition containing the present compound as an active ingredient is carried out on crop lands such as paddy fields, upland fields, orchards, etc. and also on non-crop lands.

In a first aspect of the present invention, there is provided a salt of a derivative of N-(tetrahydrobenzothiazolylcarbamoyl)oxamic acid, represented by the formula (I):

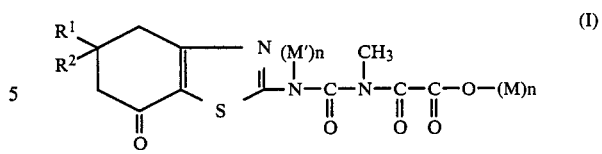

wherein $R^1$ represents a straight-chain alkyl group having up to and including six carbon atoms, branched-chain alkyl group having one to six carbon atoms, or cyclic alkyl group having up to and including six carbon atoms or a phenyl group; $R^2$ represents a hydrogen atom or a methyl group; M is an alkali metal atom or an alkaline earth metal atom; n is 1 when M is an alkali metal atom or n is ½ when M is an alkaline earth metal atom and M' represents a hydrogen atom or the same as M.

In a second aspect of the present invention, there is provided a herbicidal composition comprising as an active ingredient at least one salt of the derivative of N-(tetrahydrobenzothiazolylcarbamoyl)oxamic acid, represented by the formula (I), and a diluent therefor.

In the attached Drawing, FIGS. 1 to 13 show the infrared absorption spectra of Compounds Nos. 1 to 13 according to the present invention, respectively.

The compound according to the present invention, represented by the formula (I) is synthesized as follows.

Namely, the present compound represented by the formula (I) is obtained by reacting an alkali metal hydroxide or an alkaline earth metal hydroxide with the tetrahydrobenzothiazolylimidazolidinetrione represented by the formula (II) as follows.

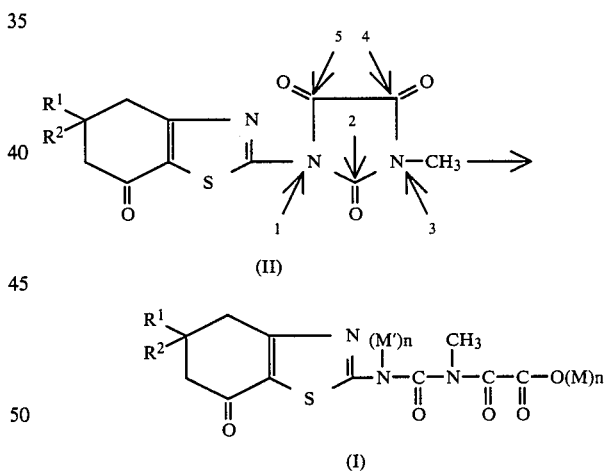

Also, by adding an aqueous solution of a salt of an alkaline earth metal to an aqueous solution of a compound represented by the formula (I) wherein M is an alkali metal, a compound represented by the formula (I) wherein M is an alkaline earth metal is obtained.

The compound represented by the formula (I) is obtained by reacting an alkali metal hydroxide with the compound represented by the formula (II) and the structure of the compound represented by the formula (I) is explained while referring to the example case wherein both $R^1$ and $R^2$ are methyl group, both M and M' are sodium and n is 1 as follows.

In the case where the compound represented by the formula (II) wherein both $R^1$ and $R^2$ are methyl group was dissolved in an aqueous acetonic solution and after adding 2 equivalent amount of aqueous dilute solution of sodium hydroxide to the solution, the whole solution was subjected to drying, thereby obtaining a water-soluble solid compound No. 6. The thus obtained compound No. 6 showed an infrared absorption spectrum indicating a typical absorption band of a salt of a carboxylic acid at 1620 cm$^{-1}$, and gave the analytical data indicating the presence of 2 atoms of sodium and 3 molecules of water of crystallization. Further, in the case where the aqueous solution of the compound No. 6 was made acidic, the compound represented by the formula (II) wherein both $R^1$ and $R^2$ are methyl group was regenerated. In the case where the compound No. 6 was methylated in hexamethylphosphorotriamide by methyl iodide, one kind of tri-methylated product, the compound No. 14, was obtained. Compound No. 14 (M.P.: 192° to 194° C.) and shows the infrared absorption bands at 1740, 1650 and 1625 cm$^{-1}$ and NMR spectral peaks at 3.25, 3.66 and 3.80 ppm which are 3H and singlet, respectively. These data indicate the presence of methyl groups bonded to three kinds of hetero atoms. In the case where the compound No. 14 was hydrolyzed by an aqueous dilute solution of potassium hydroxide, an urea compound No. 15 melting (M.P.: 226° to 227° C.) and showing the infrared absorption bands at 3370, 1640 and 1620 cm$^{-1}$ and the NMR spectral peaks at 2.85 and 3.56 ppm (each 3H and a singlet) and at 7.32 (1H, broad singlet) was obtained. The urea compound No. 15 is completely same with the urea compound obtained by reacting methyl isocyanate with the known compound No. 16.

The results verify that the compound No. 6 is the product of ring opening of positions 1 and 5 of imidazolidinetrione ring of the compound represented by the formula (II) at the hydrolysis thereof, sodium metal atom of the sodium hydroxide entering into the carboxylic group and then into the amide group both formed by the ring-opening. Namely, the compound 6 belongs to the compounds represented by the formula (I). Accordingly, the above-mentioned reaction formulae are considered as follows.

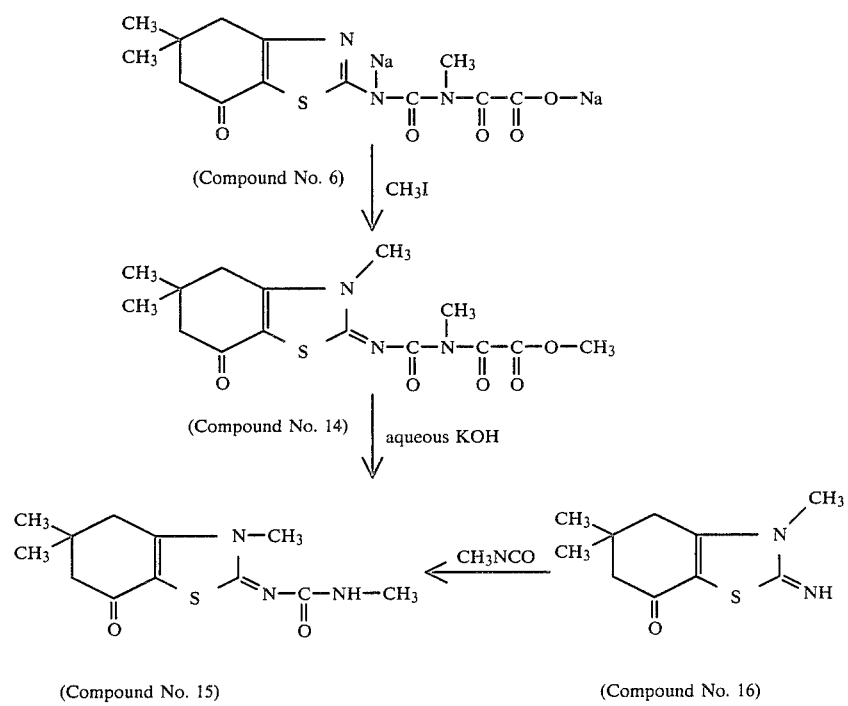

Further, since the methylation of the compound No. 16 forms the compound No. 14, in the case where M' represents a metal, a compound represented by the formula (I) is considered to be present in the form of a tautomer represented by the formula (III) or (IV) as follows.

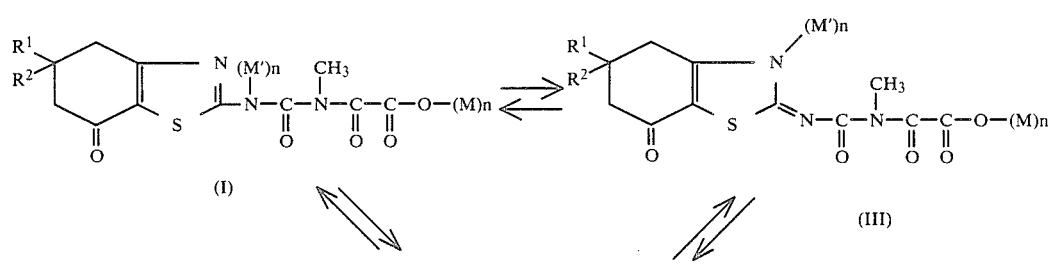

-continued

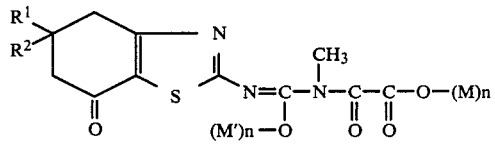

(IV)

The concrete examples of the present compounds and the physicochemical properties thereof are shown in Table 1.

NMR(D₂O)δ (ppm): 1.17 [6H, s, 5—(CH₃)₂]; 2.52 and 2.83 (each 2H, each s, 4—H and 6—H) and 3.40 (3H, s, N—CH₃).

TABLE 1

Figure 2:
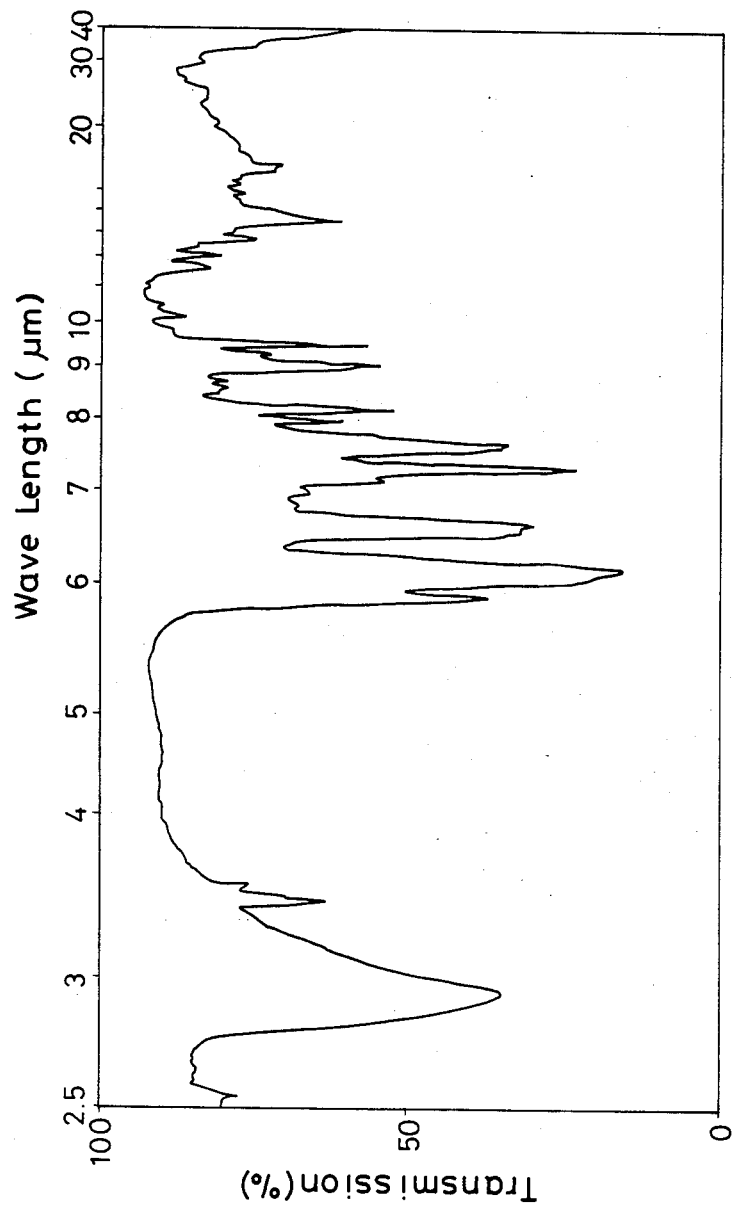
Figure 3:
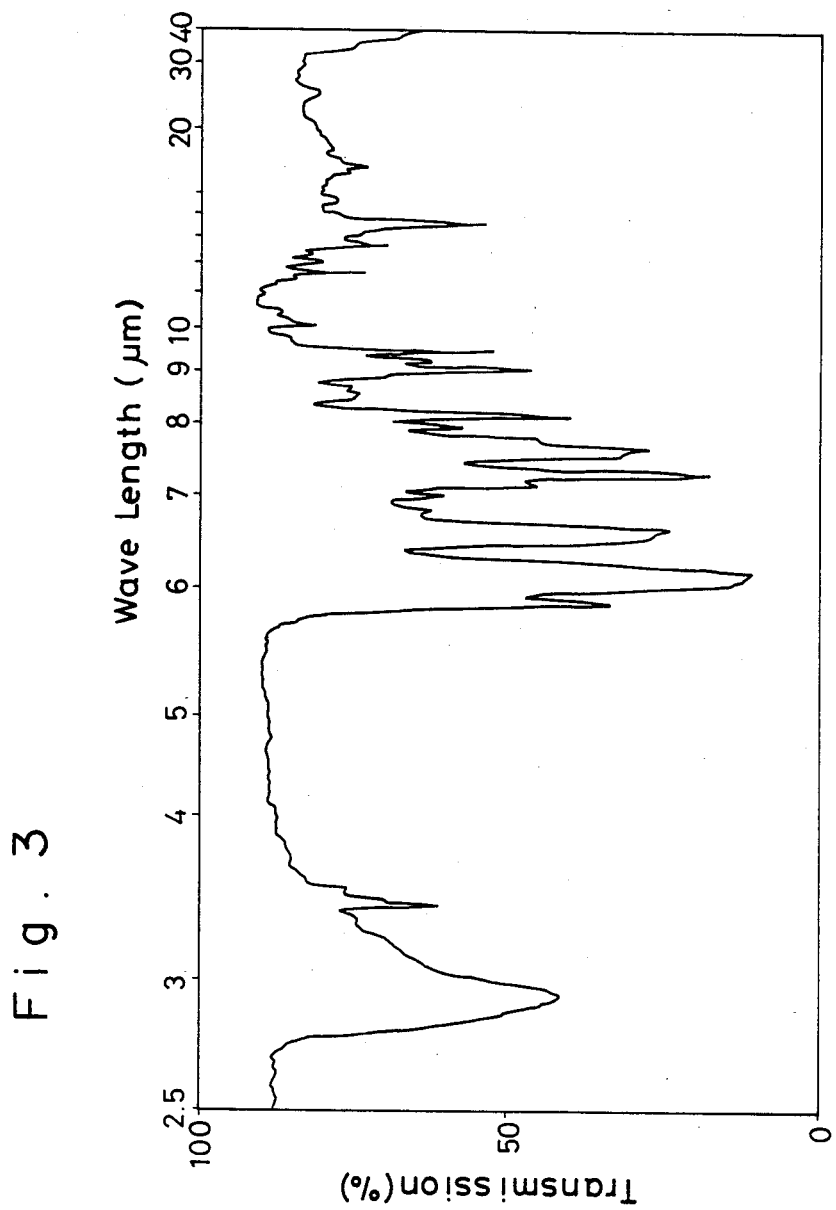
Figure 4:
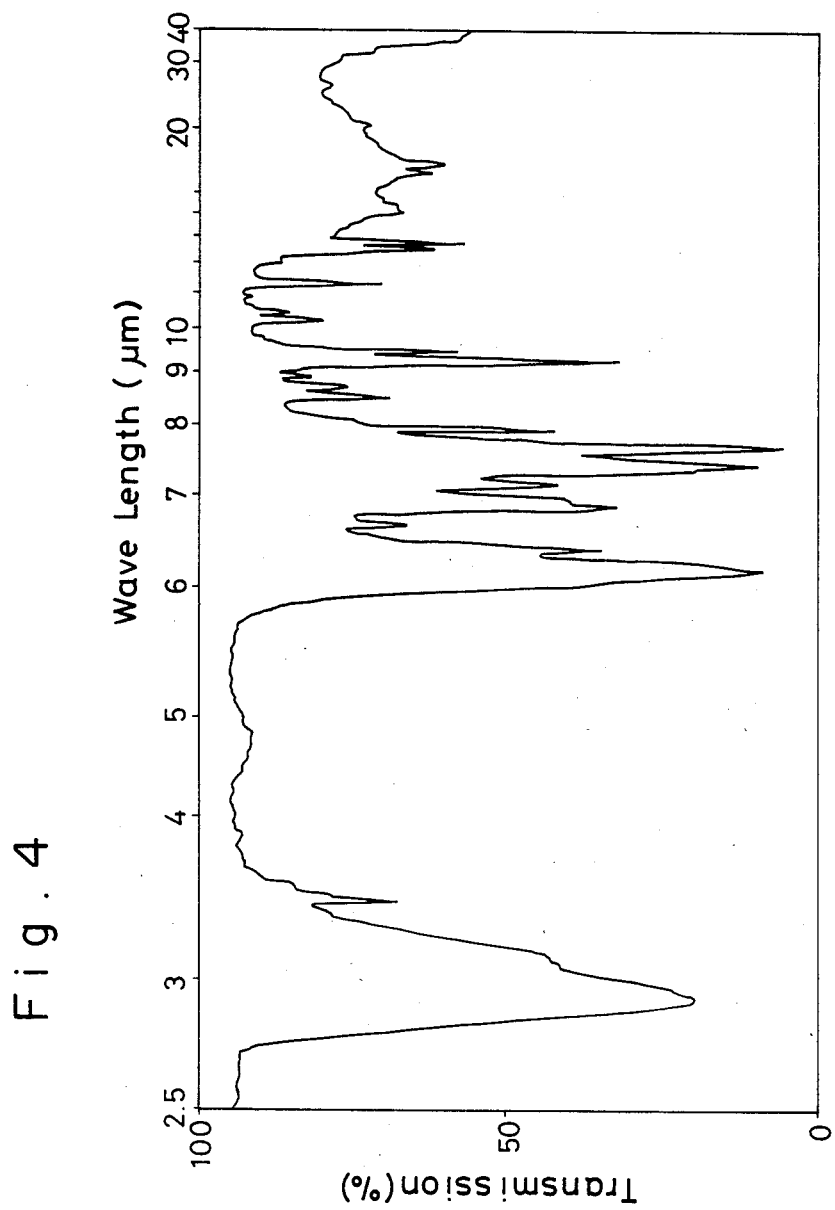
Figure 5:
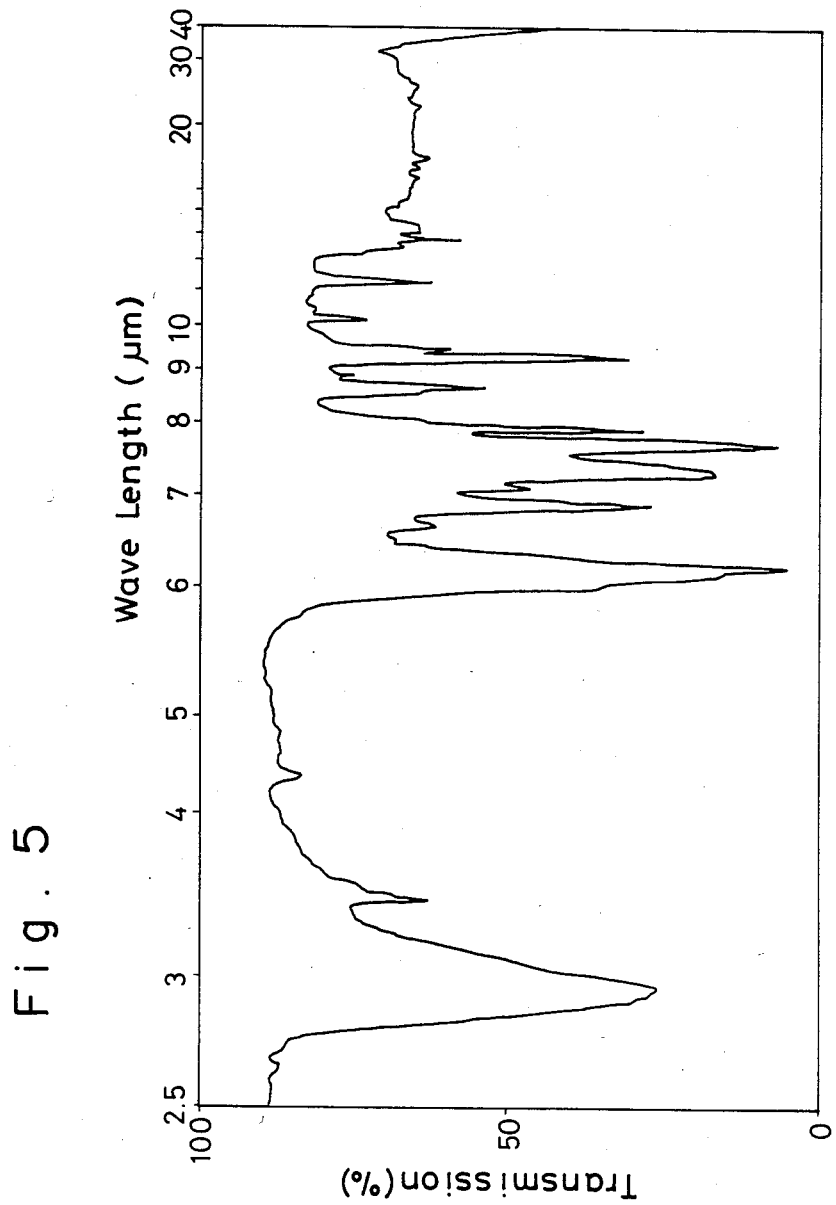
Figure 6:
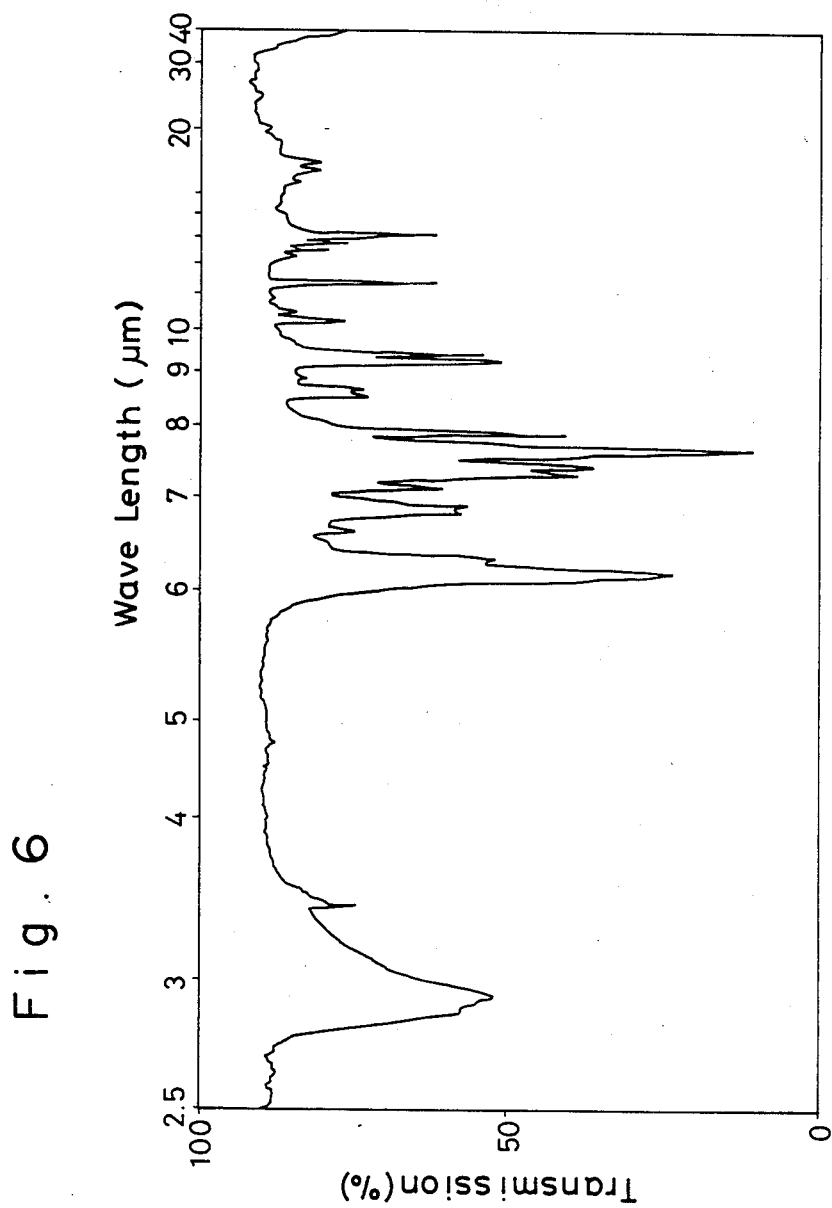
Figure 7:
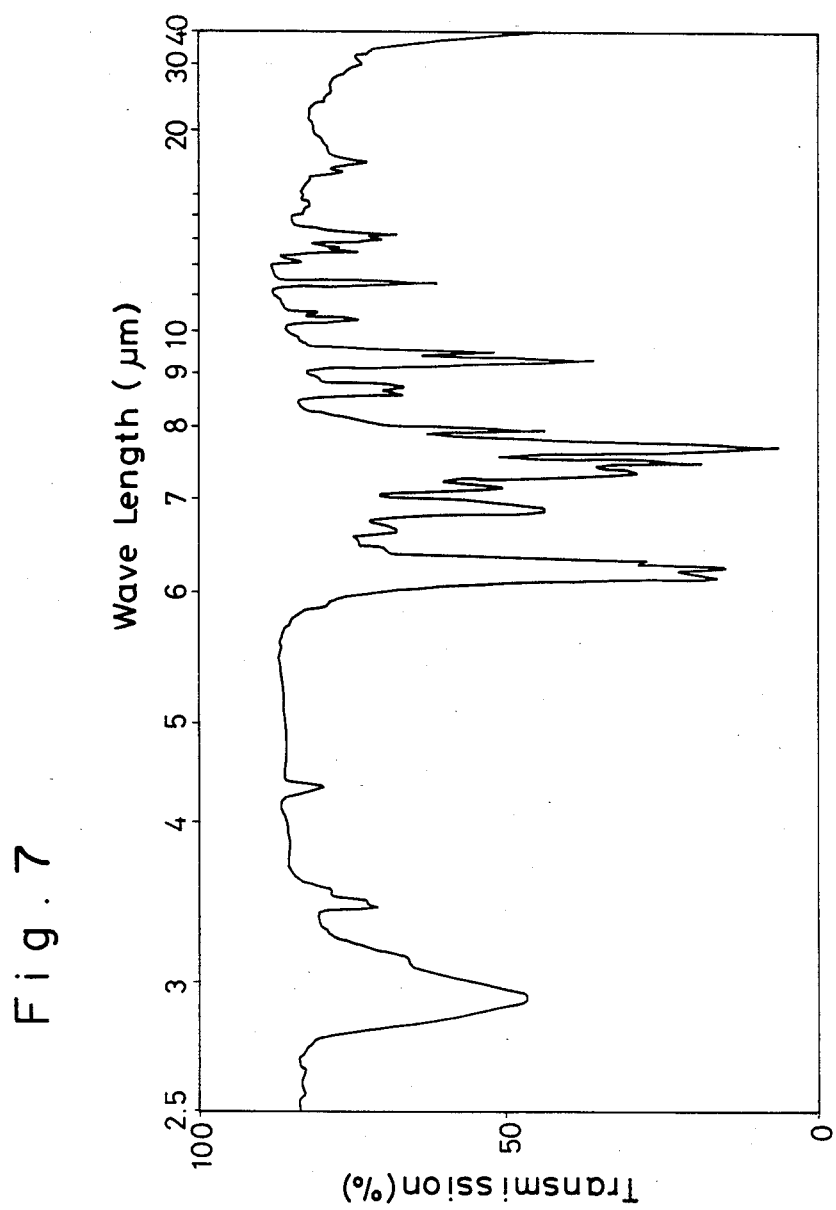
Figure 8:
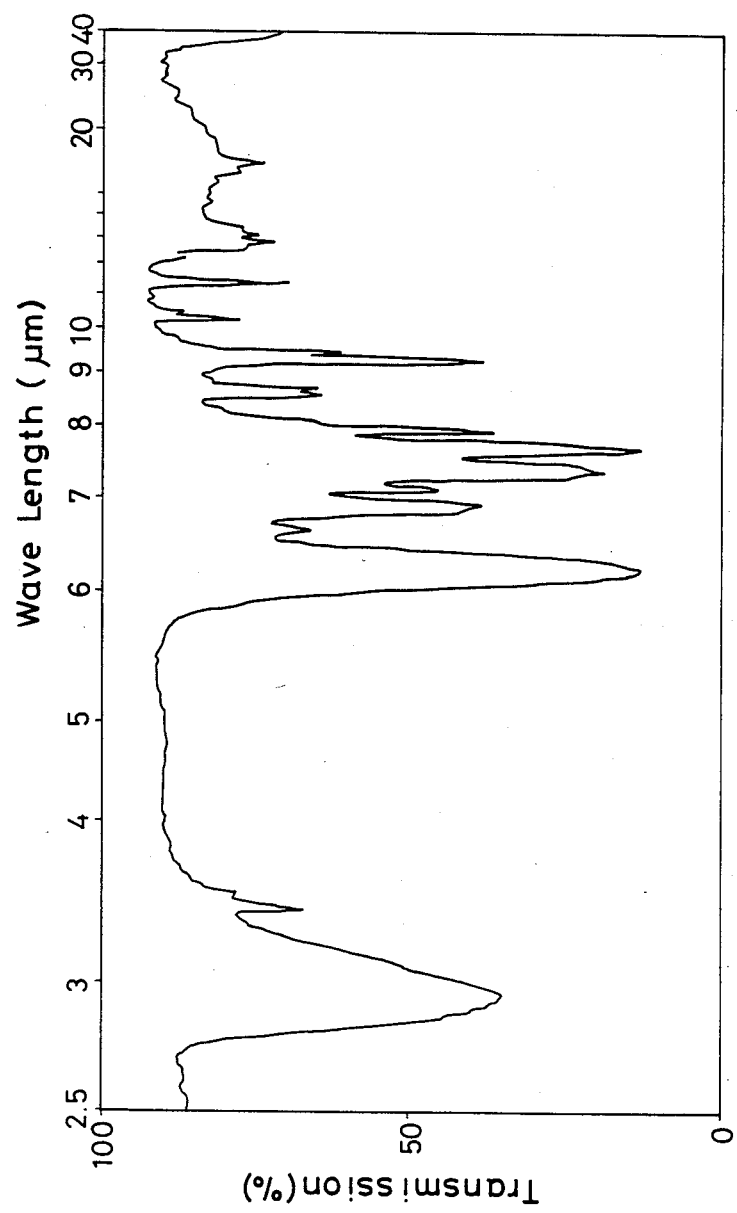
Figure 9:
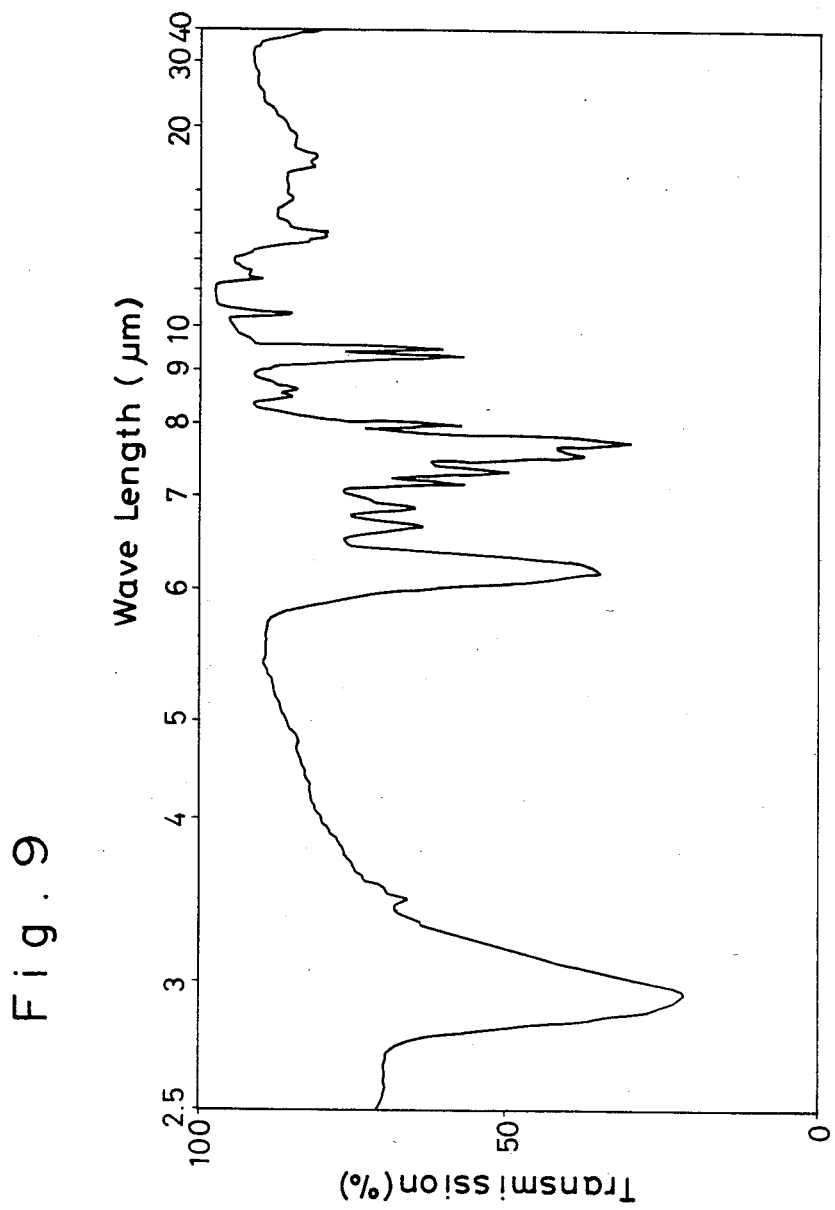
Figure 10:
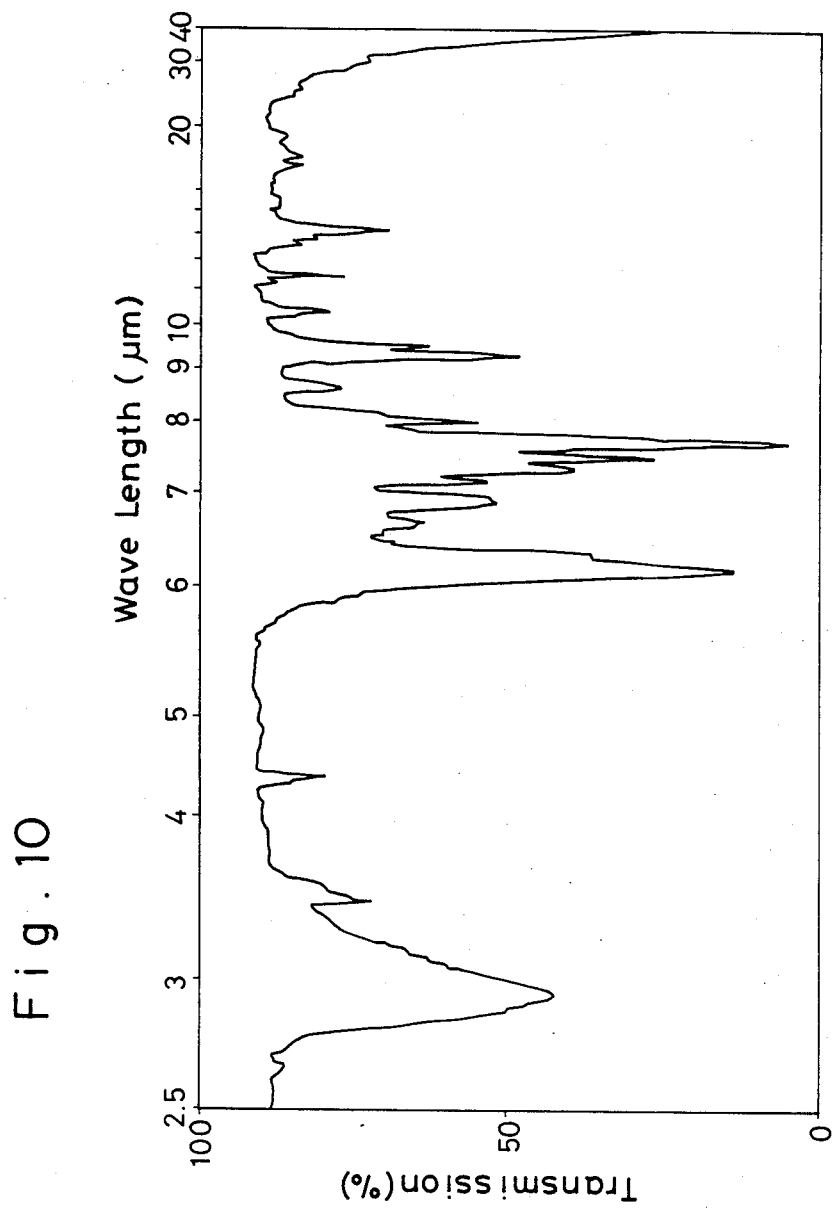
Figure 11:
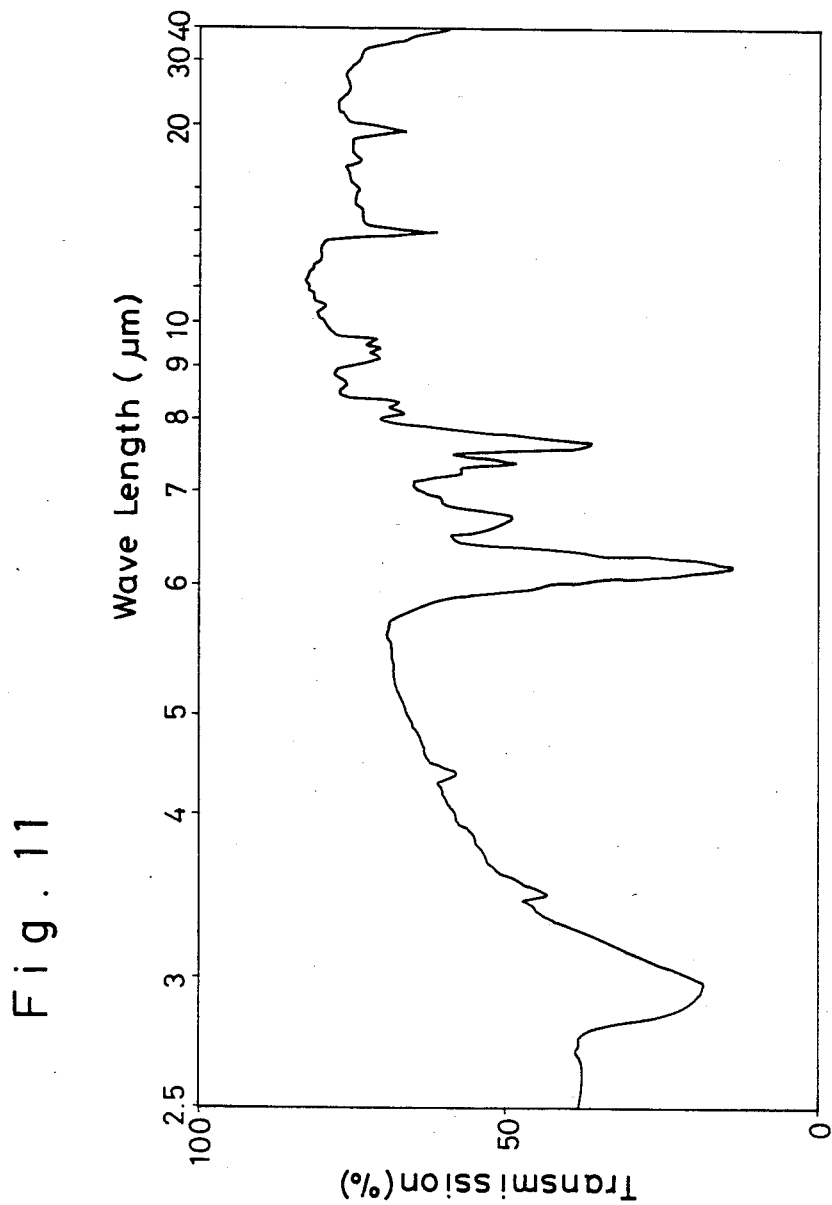
Figure 12:
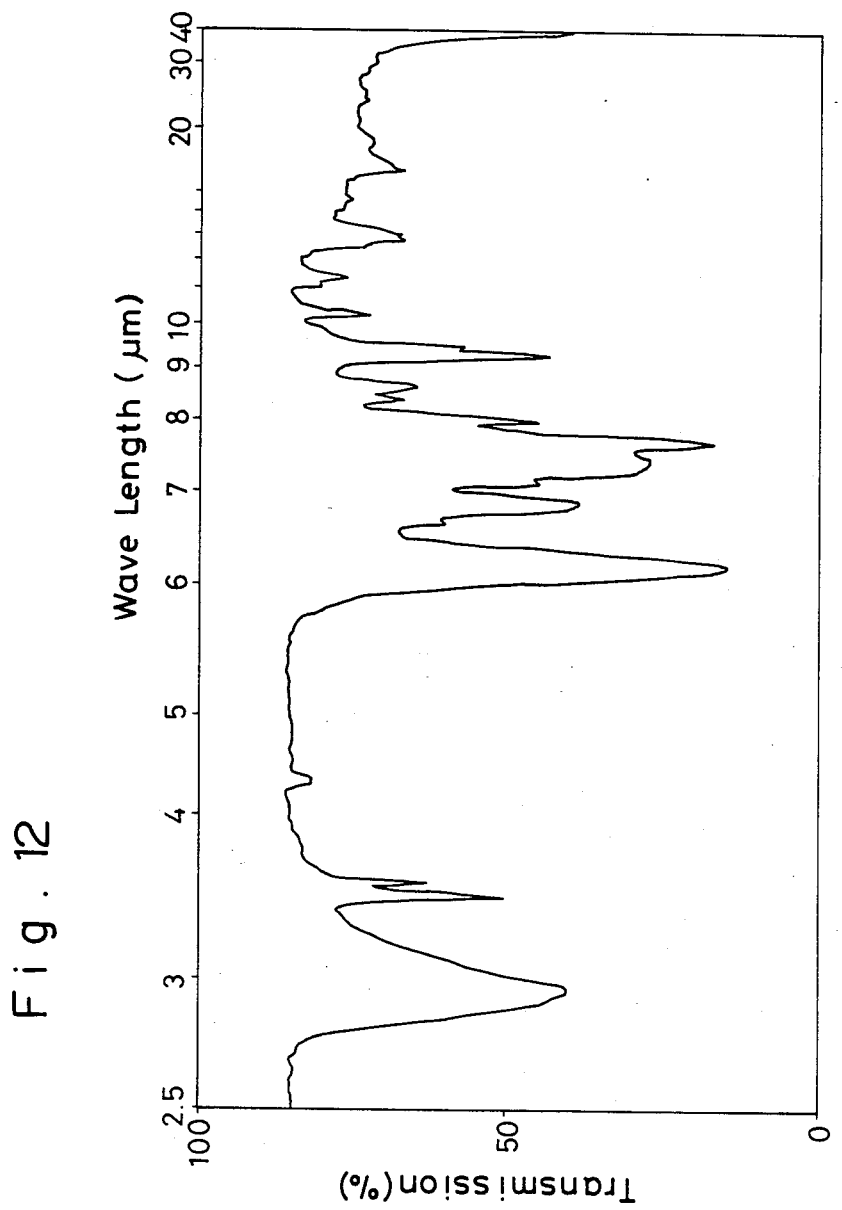
Figure 13:
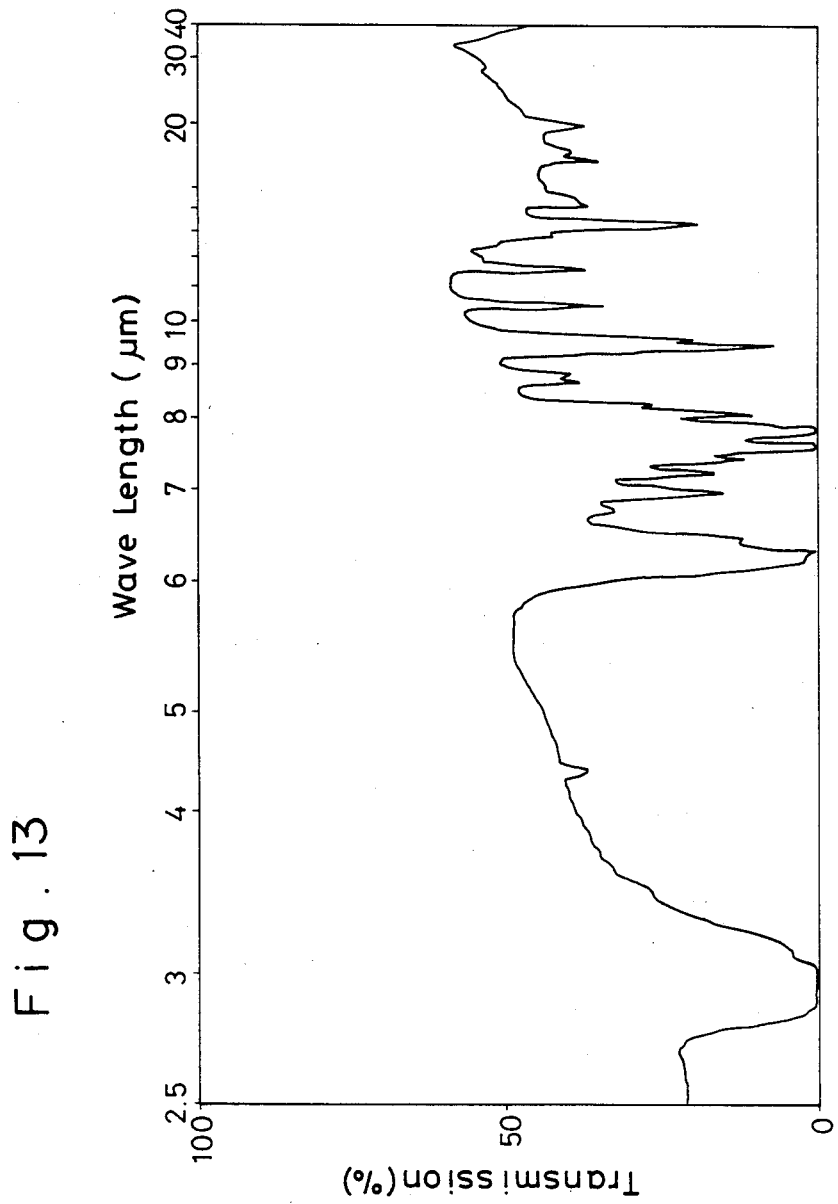

| Number of present compound | Substituent of Formula (I) | | | | Melting point (°C.) | Yield (%) | IR spectrum |
|---|---|---|---|---|---|---|---|
| | $R^1$ | $R^2$ | $(M')_n$ | $(M)_n$ | | | |
| 1 | CH₃— | CH₃— | H | Li | 205 (decomp*) | 88 | FIG. 1 |
| 2 | CH₃— | CH₃— | H | Na | 211 (decomp) | 50 | FIG. 2 |
| 3 | CH₃— | CH₃— | H | K | 211 (decomp) | 87 | FIG. 3 |
| 4 | CH₃— | CH₃— | H | Ca ½ | over 300** | 80 | FIG. 4 |
| 5 | CH₃— | CH₃— | Li | Li | 202 (decomp) | 74 | FIG. 5 |
| 6 | CH₃— | CH₃— | Na | Na | over 300 | 87 | FIG. 6 |
| 7 | CH₃— | CH₃— | K | K | 237 (decomp) | 90 | FIG. 7 |
| 8 | CH₃— | CH₃— | Ba ½ | Ba ½ | 275 (decomp) | 99 | FIG. 8 |
| 9 | CH₃— | H— | Na | Na | 260 (decomp) | 92 | FIG. 9 |
| 10 | (CH₃)₂CH— | H— | Na | Na | over 300 | 96 | FIG. 10 |
| 11 | (CH₃)₃C— | H— | Na | Na | over 300 | 95 | FIG. 11 |
| 12 | cyclohexyl | H— | Na | Na | 260 (decomp) | 90 | FIG. 12 |
| 13 | phenyl | H— | Na | Na | 290 (decomp) | 66 | FIG. 13 |

Notes:
*melts with decomposition.
**any accurate temperature of decomposition was not observed, however, browning began at about 260° C. and accordingly, the decomposition seemed to have begun.

The present invention will be more precisely explained while referring to Examples as follows.

However, the present invention is not restricted to Examples under mentioned.

EXAMPLE 1

Synthesis of Potassium N-[(4,5,6,7-tetrahydro-5,5-dimethyl-7-oxo-2-benzothiazolyl)carbamoyl]-N-methyloxamate (Compound No. 3)

In 100 ml of acetone, 1.0 g (0.0033 mol) of 1-(4,5,6,7-tetrahydro-5,5-dimethyl-7-oxo-2-benzothiazolyl)-3-methylimidazolinetrione (Compound represented by the formula (II) (wherein $R^1$ and $R^2$ denote CH₃) was dissolved, and after adding 50 ml of water to the solution, 35 ml of aqueous 0.1N solution of potassium hydroxide (0.0035 mol) were added to the aqueous solution. After condensing the aqueous solution to about 2 ml, the concentrate was dissolved in acetone, and ether was added to the solution, thereby obtaining 1.1 g of crystals [yield: 85% and M.P.: 211° C. (decomposition)], which were a hydrate of the objective compound with 1.5 mol of water of crystallization. The product showed the following elementary analytical data.

| | H₂O (%) | K (%) | C (%) | H (%) | N (%) |
|---|---|---|---|---|---|
| Found: | 6.20 | 9.97 | 39.70 | 4.02 | 10.92 |
| Calculated as C₁₃H₁₄N₃O₅SK.1.5H₂O: | 6.92 | 10.01 | 40.00 | 4.39 | 10.76 |

The product showed the following IR spectrum and NMR spectrum.
IR(KBr, cm⁻¹): $\nu_{CO}$ 1710 and 1620.

EXAMPLE 2

Synthesis of Half calcium N-[(4,5,6,7-tetrahydro-5,5-dimethyl-7-oxo-2-benzothiazolyl)carbamoyl]-N-methyloxamate (Compound No. 4)

In 100 ml of acetone, 1.0 g (0.0033 mol) of the compound represented by the formula (II) (wherein $R^1$ and $R^2$ denote CH₃) was dissolved, and after adding 50 ml of water, 70 ml of aqueous 0.1N solution of sodium hydroxide (0.007 mol) were added and then 10 ml of aqueous solution of 0.4 g of calcium chloride (0.0036 mol) were added to the solution. After stirring the mixture, the precipitated crystals were collected by filtration and washed with water and then with acetone. The thus obtained crystals contained water of crystallization of 6.5 mol, and weighed 1.2 g (yield: 80% and M.P.: over 300° C.).

The product showed the following elementary analytical data.

| | H₂O (%) | Calcium (%) | C (%) | H (%) | N (%) |
|---|---|---|---|---|---|
| Found: | 25.40 | 5.05 | 33.12 | 5.40 | 9.14 |
| Calculated as C₁₃H₁₄N₃O₅S½Ca.6.5H₂O: | 25.38 | 4.34 | 33.83 | 5.90 | 9.11 |

The product showed the IR spectrum as KBr tablet:
$\nu_{CO}$ 1640 cm⁻¹.

EXAMPLE 3

Synthesis of Disodium
N-[(4,5,6,7-tetrahydro-5,5-dimethyl-7-oxo-2-benzo-thiazolyl)carbamoyl]-N-methyloxamate (Compound No. 6)

In 100 ml of acetone, 1.0 g (0.0033 mol) of the compound represented by the formula (II) (wherein $R^1$ and $R^2$ denote $CH_3$) was dissolved, and after adding 50 ml of water to the solution, 70 ml of aqueous 0.1N sodium hydroxide solution (0.007 mol) were added to the aqueous solution and then the solution was dried to solid by removing water and acetone under a reduced pressure. The thus obtained solid material was dissolved in a small amount of water, and acetone was added to the solution to obtain crystals of trihydrate of the objective compound in an amount of 1.2 g (yield: 87%: M.P.: over 300° C.).

The product showed the following analytical data.

|  | $H_2O$ (%) | Na (%) | C (%) | H (%) | N (%) |
|---|---|---|---|---|---|
| Found: | 12.78 | 10.54 | 37.53 | 4.49 | 10.53 |
| Calculated as $C_{13}H_{13}N_3O_5SNa_2.3H_2O$: | 12.77 | 10.86 | 36.88 | 4.52 | 9.92 |

The product showed the following IR spectrum and NMR spectrum.

IR (KBr, $cm^{-1}$): $\nu_{CO}$ 1620.

NMR($D_2O$)δ (ppm): 1.06 [6H, s, 5'—$(CH_3)_2$]; 2.43 and 2.73 (each 2H, each s, 4—H and 6—H) and 3.25 (3H, s, N—$CH_3$).

EXAMPLE 4

Synthesis of Barium
N-[(4,5,6,7-tetrahydro-5,5-dimethyl-7-oxo-2-benzo-thiazolyl)carbamoyl]-N-methyloxamate (Compound No. 8)

Into 100 ml of acetone, 1.0 g (0.0033 mol) of the compound represented by the formula (II) (wherein $R^1$ and $R^2$ denote $CH_3$) was dissolved, and after adding 20 ml of water to the solution, and 20 ml of an aqueous solution of 1.3 g of barium hydroxide octahydrate (0.0041 mol) was added to the aqueous acetonic solution. After stirring the mixture, the thus precipitated crystals were collected by filtration, washed with water and then with acetone to obtain 1.6 g of the dihydrate of the objective compound (yield: 99% and M.P.: over 300° C.).

The product showed the following elementary analytical data.

|  | $H_2O$ (%) | Ba (%) | C (%) | H (%) | N (%) |
|---|---|---|---|---|---|
| Found: | 7.46 | 26.80 | 30.94 | 3.20 | 8.36 |
| Calculated as $C_{13}H_{13}N_3O_5SBa.2H_2O$: | 7.26 | 27.65 | 31.43 | 3.45 | 8.46 |

The product showed the following IR spectrum as KBr tablet: $\nu_{CO}$ 1610 $cm^{-1}$.

PREPARATION EXAMPLE 1

Preparation and application of a wettable powder

By mixing 50 parts by weight of the present compound (Compound No. 3), 5 parts by weight of a salt of ligninsulfonic acid, 3 parts by weight of a salt of alkylsulfonic acid and 42 parts by weight of diatomaceous earth and pulverizing the mixture, a wettable powder was prepared.

The thus prepared wettable powder is applied after diluting with water to a suitable concentration of the present compound (Compound No. 3) as the active ingredient.

PREPARATION EXAMPLE 2

Preparation and application of an emulsifiable concentrate

By uniformly mixing 25 parts by weight of the present compound (Compound No. 6), 65 parts by weight of xylene and 10 parts by weight of polyoxyethylenealkyl aryl ether, an emulsifiable concentrate was prepared.

The thus prepared emulsifiable concentrate is applied after diluting with water to a suitable concentration of the present compound (Compound No. 6) as the active ingredient.

PREPARATION EXAMPLE 3

Preparation and application of a granular composition

After uniformly mixing 8 parts by weight of the present compound (Compound No. 7), 40 parts by weight of bentonite, 45 parts by weight of clay and 7 parts by weight of a salt of ligninsulfonic acid, the mixture was kneaded with water and processed into granules by an extruding granulator. The granules were dried and sifted to be a product of granular composition which is directly applied.

The effectiveness of the present compounds are explained while referring to the herbicidal test example as follows.

HERBICIDAL TEST EXAMPLE

Herbicidal test by foliar application

To the follage of each of the following plants grown from their seeds under a management in a plastic planter of 180×580×150 mm in size, each of the wettable powders prepared as in Preparation Example 1 and diluted to 0.1% by weight of the active ingredient with water was sprayed by a small pressured-sprayer at a rate of 10 liters per are (100 m²). After spraying the plastic planter were placed in a green house.

After 21 days of the treatment, the state of the plants was observed to assess the damage due to the application of each of the wettable powders to find out the herbicidal activity thereof according to the following criteria:

| Criteria of herbicidal activity | |
|---|---|
| Index | Phytotoxicity |
| 0 | none |
| 1 | minute |
| 2 | slight |
| 3 | medium |
| 4 | severe |
| 5 | very severe (withered) |

| Name of the plants tested | |
|---|---|
| 1. *Echinochloa crus-galli* | 2. *Digitaria ciliaris* |
| 3. *Poa annua* | 4. *Cyperus iria* |
| 5. *Chenopodium album* | 6. *Stellaria media* |
| 7. *Cardamine flexuosa* | 8. *Portulaca oleracea* |
| 9. *Glycine max* (soybean) | 10. *Zea mays* (maize) |
| 11. *Triticum aestivum* (wheat) | |

The herbicidal activities of the present compounds thus assessed are shown in Table 2, the growth state of the plants when the present wettable powders were applied being 2 to 4 leaf-stage.

TABLE 2

| Plant | Herbicidal Activity | | | | | | | | | | | | | |
|---|---|---|---|---|---|---|---|---|---|---|---|---|---|---|
| | Present compound | | | | | | | | | | | | | |
| | 1 | 2 | 3 | 4 | 5 | 6 | 7 | 8 | 9 | 10 | 11 | 12 | 13 | not applied |
| *Echinochloa crus-galli* | 3 | 4 | 5 | 3 | 4 | 5 | 3 | 4 | 3 | 3 | 2 | 3 | 2 | 0 |
| *Digitaria ciliaris* | 3 | 4 | 4 | 3 | 4 | 4 | 2 | 3 | 4 | 2 | 1 | 3 | 2 | 0 |
| *Poa annua* | 4 | 4 | 4 | 4 | 4 | 4 | 2 | 3 | 4 | 4 | 1 | 2 | 1 | 0 |
| *Cyperus iria* | 2 | 2 | 2 | 2 | 2 | 2 | 1 | 2 | 1 | 0 | 2 | 0 | 0 | 0 |
| *Chenopodium album* | 5 | 5 | 5 | 5 | 5 | 5 | 5 | 5 | 5 | 4 | 4 | 3 | 5 | 0 |
| *Stellaria media* | 5 | 5 | 5 | 5 | 5 | 5 | 5 | 5 | 5 | 5 | 5 | 4 | 5 | 0 |
| *Cardamine flexuosa* | 5 | 5 | 5 | 5 | 5 | 5 | 5 | 5 | 4 | 5 | 4 | 4 | 4 | 0 |
| *Portulaca oleracea* | 5 | 5 | 5 | 4 | 5 | 5 | 5 | 4 | 4 | 3 | 4 | 3 | 4 | 0 |
| *Glycine max* (soybean) | 0 | 0 | 0 | 0 | 0 | 0 | 0 | 0 | 0 | 0 | 0 | 0 | 0 | 0 |
| *Zea mays* (maize) | 0 | 0 | 0 | 0 | 0 | 0 | 0 | 0 | 0 | 0 | 0 | 0 | 0 | 0 |
| *Triticum aestivum* (wheat) | 0 | 0 | 1 | 0 | 1 | 1 | 0 | 0 | 0 | 0 | 0 | 0 | 0 | 0 |

What is claimed is:

1. A salt of a derivative of N-(tetrahydrobenzothiazolylcarbamoyl)oxamic acid, represented by the formula:

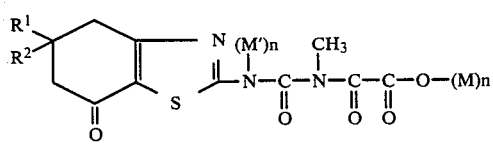
(I)

wherein $R^1$ represents a straight-chain alkyl group having one to six carbon atoms, branched-chain alkyl group having up to and including six carbon atoms, cyclic alkyl group having up to and including six carbon atoms or a phenyl group; $R^2$ represents a hydrogen atom or a methyl group; M is an alkali metal atom or an alkaline earth metal atom; n is 1 when M is an alkali metal atom or n is ½ when M is an alkaline earth metal atom and M' is a hydrogen atom or the same as M.

2. Lithium N-[(4,5,6,7-tetrahydro-5,5-dimethyl-7-oxo-2-benzothiazolyl)carbamoyl]-N-methyloxamate, represented by the formula:

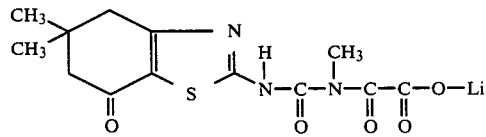

3. Sodium N-[(4,5,6,7-tetrahydro-5,5-dimethyl-7-oxo-2-benzothiazolyl)carbamoyl]-N-methyloxamate, represented by the formula:

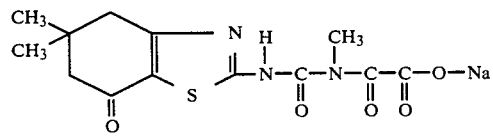

4. Potassium N-[(4,5,6,7-tetrahydro-5,5-dimethyl-7-oxo-2-benzothiazolyl)carbamoyl]-N-methyloxamate, represented by the formula:

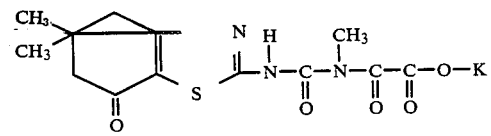

5. Dilithium N-[(4,5,6,7-tetrahydro-5,5-dimethyl-7-oxo-2-benzothiazolyl)carbamoyl]-N-methyloxamate, represented by the formula:

6. Disodium N-[(4,5,6,7-tetrahydro-5,5-dimethyl-7-oxo-2-benzothiazolyl)carbamoyl]-N-methyloxamate, represented by the formula:

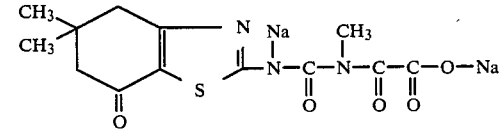

7. A herbicidal composition comprising as an active ingredient, a salt of a derivative of N-(tetrahydrobenzothiazolylcarbamoyl)oxamic acid, represented by the formula:

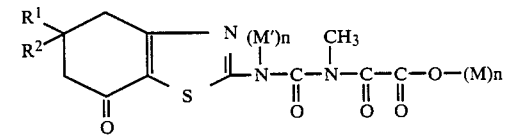

wherein $R^1$ represents a straight-chain alkyl group having one to six carbon atoms, branched-chain alkyl group having up to and including six carbon atoms, cyclic alkyl group having up to and including six carbon atoms, or a phenyl group; $R^2$ represents a hydrogen atom or a methyl group; M is an alkali metal atom or an alkaline earth metal atom; n is 1 when M is an alkali metal atom or n is ½ when M is an alkaline earth metal atom and M' is a hydrogen atom or the same as M.

8. A herbicidal composition according to claim 7, wherein said salt of the derivative is lithium N-[(4,5,6,7- tetrahydro-5,5-dimethyl-7-oxo-2-benzothiazolyl)carbamoyl]-N-methyloxamate, represented by the formula:

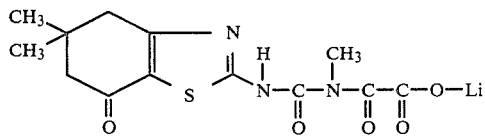

9. A herbicidal composition according to claim 7, wherein said salt of the derivative is sodium N-[(4,5,6,7-tetrahydro-5,5-dimethyl-7-oxo-2-benzothiazolyl)carbamoyl]-N-methyloxamate, represented by the formula:

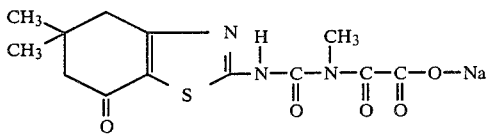

10. A herbicidal composition according to claim 7, wherein said salt of the derivative is potassium N-[(4,5,6,7-tetrahydro-5,5-dimethyl-7-oxo-2-benzothiazolyl)carbamoyl]-N-methyloxamate, represented by the formula:

11. A herbicidal composition according to claim 7, wherein said salt of the derivative is dilithium N-[(4,5,6,7-tetrahydro-5,5-dimethyl-7-oxo-2-benzothiazolyl)carbamoyl]-N-methyloxamate, represented by the formula:

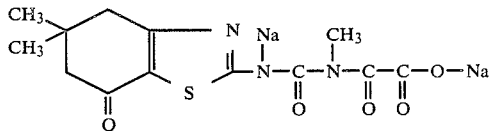

12. A herbicidal composition according to claim 7, wherein said salt of the derivative is disodium N-[(4,5,6,7-tetrahydro-5,5-dimethyl-7-oxo-2-benzothiazolyl)carbamoyl]-N-methyloxamate, represented by the formula:

* * * * *

UNITED STATES PATENT AND TRADEMARK OFFICE
CERTIFICATE OF CORRECTION

PATENT NO. : 4,549,902

DATED : 10/29/85

INVENTOR(S) : A. Aoki; T. Shida; H. Arabori; S. Kumazawa; S. Shimizu; T. Watanabe; Y. Kanda; K. Satake; S. Yamazaki; H. Shinkawa; and T. Chida.

It is certified that error appears in the above-identified patent and that said Letters Patent is hereby corrected as shown below:

Column 10, line 25, delete the following formula:

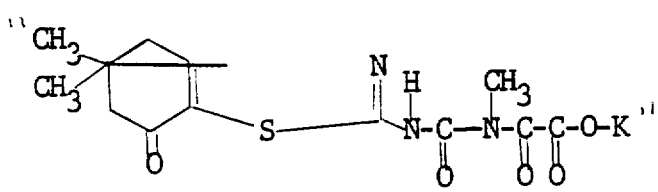

and substitute the following formula:

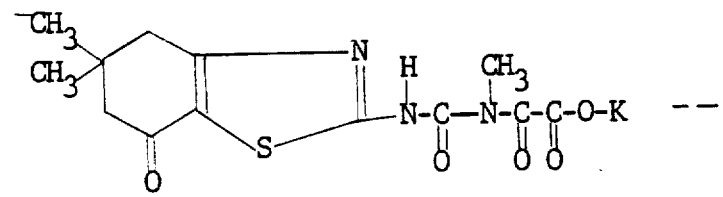

Signed and Sealed this

Fourteenth Day of April, 1987

*Attest:*

DONALD J. QUIGG

*Attesting Officer*    *Commissioner of Patents and Trademarks*